US009694198B2

(12) United States Patent
Brown

(10) Patent No.: US 9,694,198 B2
(45) Date of Patent: Jul. 4, 2017

(54) METHOD AND APPARATUS FOR DISTINGUISHING RADIATION EMITTED BY TARGETS AND NON-TARGETS DURING SURGICAL LASER PROCEDURES

(76) Inventor: Joe Denton Brown, Panama City, FL (US)

( * ) Notice: Subject to any disclaimer, the term of this patent is extended or adjusted under 35 U.S.C. 154(b) by 158 days.

(21) Appl. No.: 14/234,246

(22) PCT Filed: Jul. 19, 2012

(86) PCT No.: PCT/US2012/047300
§ 371 (c)(1),
(2), (4) Date: Apr. 8, 2014

(87) PCT Pub. No.: WO2013/012986
PCT Pub. Date: Jan. 24, 2013

(65) Prior Publication Data
US 2014/0225006 A1   Aug. 14, 2014

Related U.S. Application Data

(60) Provisional application No. 61/509,523, filed on Jul. 19, 2011, provisional application No. 61/599,033, filed on Feb. 15, 2012.

(51) Int. Cl.
| G01N 21/64 | (2006.01) |
| A61N 5/06 | (2006.01) |
| A61B 18/20 | (2006.01) |
| A61B 18/00 | (2006.01) |
| A61B 90/00 | (2016.01) |

(52) U.S. Cl.
CPC ............. *A61N 5/06* (2013.01); *A61B 18/20* (2013.01); *A61B 2018/0066* (2013.01); *A61B 2018/00904* (2013.01); *A61B 2090/3941* (2016.02)

(58) Field of Classification Search
USPC ....................................... 250/459.1
See application file for complete search history.

(56) References Cited

U.S. PATENT DOCUMENTS

| 5,409,481 | A | * | 4/1995 | Poppas et al. ................. 606/12 |
| 5,704,890 | A | * | 1/1998 | Bliss ................. A61N 5/1048 600/1 |
| 5,928,222 | A | * | 7/1999 | Kleinerman ................. 606/16 |
| 6,636,686 | B1 | * | 10/2003 | Belfer ............... G02B 6/0003 362/554 |
| 6,671,540 | B1 | * | 12/2003 | Hochman .................... 600/431 |
| 2005/0136486 | A1 | * | 6/2005 | Haushalter ............. B82Y 5/00 435/7.2 |
| 2006/0263908 | A1 | * | 11/2006 | Hirai ......................... 436/526 |
| 2008/0033300 | A1 | * | 2/2008 | Hoang et al. ............... 600/474 |
| 2008/0161827 | A1 | * | 7/2008 | Frost ......................... 606/116 |
| 2011/0021970 | A1 | * | 1/2011 | Vo-Dinh et al. ............ 604/20 |

(Continued)

FOREIGN PATENT DOCUMENTS

WO   WO 2010053575 A2 *  5/2010  ............. A61B 18/22

*Primary Examiner* — Kiho Kim
(74) *Attorney, Agent, or Firm* — Bacon & Thomas, PLLC

(57) ABSTRACT

Methods and arrangements for distinguishing between target areas and non-target areas during a laser surgical procedure involve coating or otherwise providing the non-target areas with a phosphorescent material that emits radiation, upon stimulation when a predetermined condition occurs, that is distinguishable from the treatment radiation.

19 Claims, 2 Drawing Sheets

(56) References Cited

U.S. PATENT DOCUMENTS

| | | | |
|---|---|---|---|
| 2012/0064134 A1* | 3/2012 | Bourke, Jr. | A61Q 17/04 |
| | | | 424/401 |
| 2012/0123205 A1* | 5/2012 | Nie et al. | 600/109 |
| 2013/0197480 A1* | 8/2013 | McDaniel | 604/522 |
| 2013/0218147 A1* | 8/2013 | Brown | A61B 18/22 |
| | | | 606/16 |

* cited by examiner

100 — COATING OR OTHERWISE PROVIDING THE NON-TARGET AREAS WITH A PHOSPHORESCENT MATERIAL OR PHOSPHOR THAT EMITS RADIATION AT WAVELENGTHS OR FREQUENCIES DISTINGUISHABLE FROM THOSE OF THE TREATMENT RADIATION

200 — DETECTING EMISSIONS FROM THE PHOSPHOR THAT ARE INDICATIVE OF OVERHEATING, EXCESS ENERGY ABSORPTION, OR OTHER CONDITIONS TO BE MONITORED DURING THE SURGICAL PROCEDURE.

*FIG. 1*

METHOD AND APPARATUS FOR DISTINGUISHING RADIATION EMITTED BY TARGETS AND NON-TARGETS DURING SURGICAL LASER PROCEDURES

This application claims the benefit of Provisional U.S. Patent Appl. Ser. Nos. 61/509,523, filed Jul. 19, 2012, and 61/599,033, filed Feb. 2, 2015.

BACKGROUND OF THE INVENTION

1. Field of the Invention

The invention relates to methods and arrangements for distinguishing between target areas and non-target areas during a laser surgical procedure, by coating or otherwise providing the non-target areas with a phosphorescent material or phosphor.

The target areas may be any tissue or object at which the laser is directed. The non-target areas to which the phosphors are applied may include, but are not limited to, any portion of a scope or laser delivery apparatus, including a laser sheath, buffer material of the fiber, endoscope working channel, and cardiac or urological stents, as well as tissues in the vicinity the target.

The phosphors applied to or providing in the non-target areas include any materials that, when exposed to a particular wavelength, emit light at a different wavelength. In one embodiment, the phosphors may be rare-earth nanophosphors that up-convert IR wavelengths to visible or near visible wavelengths, and therefore provide a detectable indication of overheating in the area of the target.

However, the invention is not limited to up-conversion of IR wavelengths, or to emissions in the visible or near visible wavelengths, but also may include materials that down-convert higher wavelengths to visible or near visible, and to phosphors that emit IR or UV rather than visible or near-visible radiation. The phosphors may also be used for monitoring purposes other than overheating detection. For example, phosphors may be included in the fiber itself, and in particular the cladding and/or buffer, to be used as an indicator of excess energy absorption in the cladding or buffer. Furthermore, multiple different types of phosphors may be provided in a particular application to carry out different monitoring functions.

The phosphor emissions may be monitored in a variety ways, including automated wavelength or frequency detection, as well as observation of visible wavelengths by an operator or clinician. In addition, analysis techniques may include frequency domain (Fourier) analysis and other complex signal analyzing techniques.

2. Description of Related Art

Copending U.S. patent application Ser. No. 13/127,911 (PCT Pub. WO 2010/053575) describes feedback systems described therein are used in connection with sacrificial elements or coatings that absorb selected wavelengths of radiation emitted during a surgical procedure, and that in response heat up or emits radiation in a way that can more easily and reliably be detected by the treatment site monitoring arrangement. The present invention is based on similar principles, but the phosphors of the present invention are not intended to be sacrificed, but rather are detected based solely on frequency conversion or fluorescence signature.

Copending U.S. patent application Ser. No. 13/070,247 (U.S. Pub. 2011/0238048) is also of interest since it discloses distinguishing radiation emitted as a result of fiber breakdown from radiation reflective of a normal surgical procedure based on radiation event counts. The present application provides an alternative and more versatile way of distinguishing between events, although it can also be combined with the count procedure of the copending application.

In addition to disclosure of various techniques and arrangements for distinguishing between target and non-target emissions at a treatment site, the inventor has proposed a variety of treatment-monitoring feedback systems that can detect the wavelength, amplitude, or timing of radiation that originate at the surgical site, including feedback systems capable of analyzing the frequency spectrum of emissions. Examples of feedback systems that can be used with the method and apparatus of the invention are described in copending U.S. patent application Ser. Nos. 11/714,785 (U.S. Pub. 2007/0167937), 12/073,922 (U.S. Pub. 2009-0149845), 13/070,247, and 13/127,911 (PCT Pub. WO 2010/053575), each of which is incorporated by reference herein.

SUMMARY OF THE INVENTION

A method for distinguishing between target areas and non-target areas during a laser surgical procedure involves coating or otherwise providing the non-target areas with a phosphorescent material or phosphor that emits radiation at wavelengths or frequencies distinguishable from those of the treatment radiation, and detecting emissions from the phosphor that are indicative of overheating, excess energy absorption, or other conditions to be monitored during the surgical procedure.

The target areas may be any tissue or object at which the laser is directed. The non-target areas to which the phosphors are applied may include, but are not limited to, any portion of a scope or laser delivery apparatus, including a laser sheath, buffer material of the fiber, endoscope working channel, and cardiac or urological stents, as well as tissues in the vicinity the target. The invention includes the parts of the scope or laser delivery apparatus that have been coated or treated with phosphors, or that include phosphors within the material of the respective parts, as well as to the coatings and/or treatments by which the phosphors are applied at the treatment site.

Those skilled in the art will appreciate that the invention relates not only to a method, but also to laser delivery devices, scopes, or other apparatus that have been painted or coated with a rare-earth phosphor of the type described herein, and in particular that can down convert up convert selected wavelengths, and/or that exhibit auto-fluorescence for an interval that is easily distinguishable from that of a non-painted or coated target. In addition, the invention relates to any sort of marker that has been painted, coated, or otherwise provided with rare-earth fluorescent nanophosphors of the type described herein.

According to a preferred embodiment of the invention, the method involves painting the non-target area with a rare-earth phosphor that can up convert IR wavelengths to visible or near visible wavelengths, and that therefore provides a detectable indication of overheating in the area of the target. Alternatively, or in addition to the use or up converting rare-earth fluorescent nanophosphors, the invention can utilize rare-earth fluorescent nanophosphors that down-convert wavelengths to visible or near visible, and/or that exhibit auto-fluorescence for an interval that is easily distinguishable from that of a non-painted area. Furthermore, to distinguish non-target tissues where painting or coating is not a viable option, the phosphors may be applied to a marker that can be positioned in the area of the non-target tissues.

Examples of phosphors suitable for use in the method of the invention are the rare-earth fluorescent nanophosphors described in the article *SPIE Newsroom, DOI:* 10.1117/2.2201009.0001 (Sep. 17, 2010), which up-convert from near-IR to visible wavelengths, incorporated by reference herein. Different phosphors may be used simultaneously to indicate the occurrence of different types of events that might require different responses on the part of the clinician.

In addition to visual observation of emissions by a clinician, for example, by looking for characteristic colors of light emitted by the phosphors, the method and phosphor coated/treated parts of the invention may be used in connection with any automated feedback system capable of detecting the wavelength, amplitude, timing, or signature (pattern) of radiation that originate at the surgical site, and in particular that are capable of detecting wavelengths emitted by the phosphor. Examples of feedback systems that can be used with the method and apparatus of the invention include those described in the above-cited copending U.S. patent application Ser. Nos. 11/714,785 (U.S. Pub. 2007/0167937), 12/073,922 (U.S. Pub. 2009-0149845), 13/070,247, and 13/127,911 (PCT Pub. WO 2010/053575), each of which is incorporated by reference herein.

BRIEF DESCRIPTION OF THE DRAWINGS

FIG. 1 is a flowchart illustrating a preferred method of distinguishing between target and non-target areas.

DETAILED DESCRIPTION OF THE PREFERRED EMBODIMENTS

Figure 2:
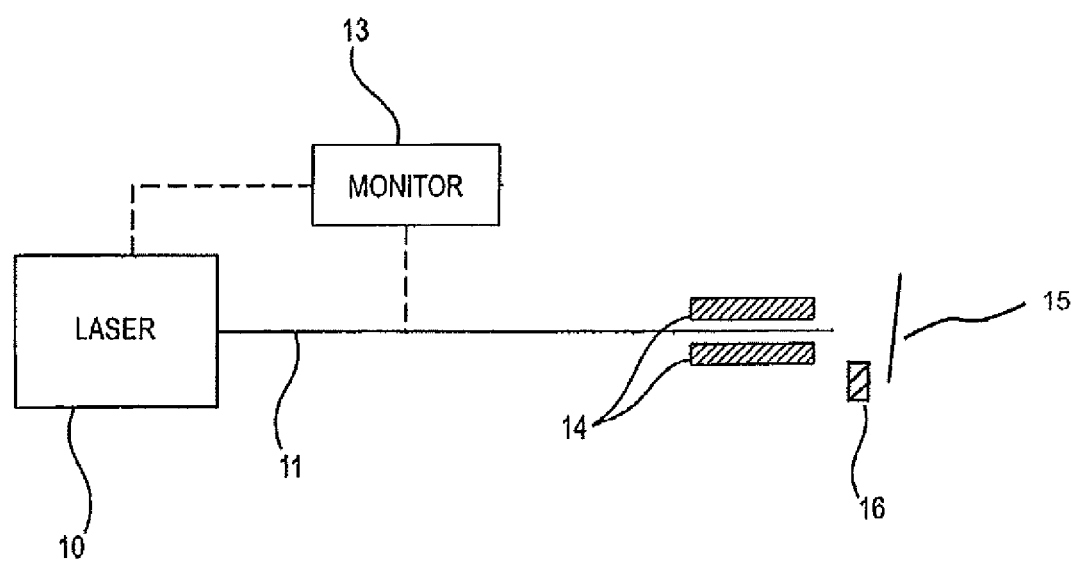
FIG. 2 is a schematic diagram illustrating parts that may be coated or treated with phosphors according a preferred embodiment of the invention.

As illustrated in FIG. 1, the method of a preferred embodiment of the invention includes the step 100 of coating or otherwise providing non-target areas at a treatment site with a phosphor that emits radiation at wavelengths or frequencies distinguishable from those of the treatment radiation. This step may be accomplished by coating parts of the surgical instrument, introducer, or fiber with a material containing a phosphor, by including the phosphor in the material of the surgical instrument, introducer, or fiber, by coating non-target tissues at the treatment site with the phosphor-containing material, or by providing a phosphor-containing marker near the target.

The phosphor may be a rare-earth nano-phosphor, or any other material that emits light at predetermined frequencies or wavelengths in response to stimulation by incident light or radiation within a characteristic frequency or wavelength range. For example, if the stimulation wavelengths are infrared wavelengths, then the emissions, which may be but are not limited to visible or near-visible wavelength emissions, can be used to provide an indication of temperature. If the emissions are visible wavelengths, then the color associated with the wavelengths can provide an easily discernible indication of overheating to a clinician viewing the treatment site through a scope. Alternatively, phosphors within the cladding or buffer of a fiber may emit light of any detectable wavelength in response to excess radiation capture by the cladding or buffer so as to provide a warning of problems with the fiber itself.

Step 200 of the method illustrated in FIG. 1 is the detection step, which involves detection of emission from the phosphor that are indicative of overheating, excess energy absorption, or other conditions to be monitored at the treatment sited during a surgical procedure. As noted above, the invention may be used with feedback detection apparatus such as those described in copending U.S. patent application Ser. Nos. 11/714,785 (U.S. Pub. 2007/0167937), 12/073,922 (U.S. Pub. 2009-0149845), 13/070,247, and 13/127,911 (PCT Pub. WO 2010/053575), and may involve detection of emissions based not only on frequency or wavelength, but also on timing or pattern. For example, the "phosphor" materials may include materials that exhibit auto-fluorescence for specific intervals that are detectable from those of background or treatment radiation. In cases where the background or treatment radiation is not easily distinguishable, or where multiple different phosphor materials are employed to monitor different conditions at the treatment site, more complex analysis techniques, such as Fourier analysis, may be used to detect emissions from the phosphor material(s).

Since the rare-earth fluorescent nanophosphors used by the present invention can emit light in visible wavelengths, however, light from the phosphors may advantageously also be detected by visual observation by a clinician. In particular, the phosphor may be selected to fluoresce with a particular color that is easily detectable by the observer, even against a bright background of glowing target tissues. For example, non-target laser delivery device breakdowns can be indicated by a red glow to indicate to the clinician that the laser needs to be paused or modulated. On the other hand, markers that fluoresce in a blue wavelength may be placed near adjacent non-target tissues to warn the clinician or operator that the non-target tissues are being affected, to assist the clinician in properly aiming the laser.

FIG. 2 is a schematic representation of an arrangement for carrying out the method of the invention. Treatment radiation is provided by a laser 10 through a fiber 11. Monitoring is optionally provided by monitor 13, which may detect light carried from the treatment site to the monitor 13 by a scope, introducer, or fiber (including possibly the fiber used to carry the treatment radiation), or electrical signals from a sensor, detector, camera, or the like at the treatment site. Monitoring may also be carried out by the clinician viewing the treatment site using conventional apparatus, but with indication of overheating or other conditions at the treatment site being given by observable changes in the view of the treatment site, such as changes in color that result from phosphor emissions.

Element 14 in FIG. 2 represents any part of a surgical instrument, introducer, scope, laser delivery device, sheath, fiber, or other apparatus, device, or part present at the treatment site and to which one or more phosphors have been applied by coating, painting, inclusion in the material of the part, or the like. Element 15 schematically represents the target tissue, while element 16 represents a coated or painted non-target tissue or a marker that has been painted, coated, or otherwise provided with a phosphor, such as a rare-earth fluorescent nano-phosphor, of the type described herein.

Having thus described and illustrated preferred embodiments of the invention, it will be appreciated that the invention is not to be limited to the specific embodiments described and illustrated herein.

I claim:

1. A method of distinguishing between radiation originating from a surgical laser target and radiation emitted by at least one non-target, comprising the steps of:

situating a phosphor at or near a treatment site by painting, coating, or mixing the phosphor with a material of a cladding or buffer of an optical fiber through which treatment radiation is directed at the surgical laser target, said phosphor emitting light at visible, near visible, or infrared wavelengths when stimulated by excess energy in the fiber cladding or buffer;

performing a treatment procedure by directing the treatment radiation at the surgical laser target through the optical fiber; and detecting, either manually or by a detector, the emission of light by the phosphor material.

2. A method as claimed in claim 1, wherein said phosphor is stimulated by infrared radiation to detect overheating.

3. A method as claimed in claim 1, wherein said emission by said phosphor is detected by frequency spectrum analysis.

4. A method of distinguishing between radiation originating from a surgical laser target and radiation emitted by at least one non-target, comprising the steps of:

performing a treatment procedure by directing a laser at the surgical laser target through an optical fiber;

situating a phosphor at or near the treatment site by painting, coating, or mixing the phosphor with a material of an instrument separate from said optical fiber, said phosphor emitting light at visible, near visible, or infrared wavelengths when stimulated; and detecting, either manually or by a feedback device, the emission of light by the phosphor material.

5. A method of distinguishing between radiation originating from a surgical laser target and radiation originating from at least one non-target, comprising the steps of:

painting, coating, or otherwise providing an instrument separate from an optical fiber for directing a laser at the surgical laser target, said instrument being introduced into a patient during a treatment procedure with a rare earth phosphor, or mixing the rare earth phosphor with a material of a cladding or buffer of the optical fiber, said phosphor emitting radiation in response to radiation originating from the non-target upon the occurrence of overheating or excess energy absorption by or in the vicinity of the non-target;

wherein the rare-earth phosphor up-converts or down-converts wavelengths of the radiation emitted by the surgical laser target, and/or changes a timing of said radiation emitted by the surgical laser target, so as to enable said radiation originating from the non-target to be more easily distinguished from said radiation emitted by the surgical laser target.

6. A method as claimed in claim 5, wherein said phosphor up-converts radiation from IR to visible.

7. A method of distinguishing between treatment radiation originating from a surgical laser target and radiation emitted by a non-target, comprising the step of:

performing a treatment procedure by inserting an optical fiber through an introducer and directing laser light at the surgical laser target through the optical fiber; and selectively monitoring wavelengths of the radiation emitted by the rare earth phosphor, detecting, by a feedback device, fluorescence emitted by a cladding or buffer of the optical fiber or by the introducer or an instrument that is separate from said optical fiber and introduced into a patient during the treatment procedure, said introducer, instrument, cladding, or buffer having been painted, coated, or otherwise provided with a phosphor, wherein the phosphor up-converts or down-converts wavelengths of the radiation originating from the non-target, and/or changes a timing of said radiation originating from the non-target, so as to enable said radiation originating from the non-target to be more easily distinguished from said radiation originating from the surgical laser target.

8. A method as claimed in claim 7, wherein said phosphor up-converts radiation from IR to visible.

9. A method of distinguishing between radiation originating from a surgical laser target and radiation emitted by a non-target, comprising the step of:

a clinician performing a treatment procedure by inserting an optical fiber through an introducer and directing laser light at the surgical laser target through the optical fiber; and the clinician using his vision to observe fluorescence emitted by a phosphor painted, coated, or otherwise provided in or on a cladding or buffer of the optical fiber or an instrument that is separate from said optical fiber and introduced into a patient during the treatment procedure, wherein the phosphor up-converts or down-converts wavelengths of the radiation emitted by said non-target to visible wavelengths so that said radiation emitted by the non-target may be more easily distinguished or observed.

10. A method as claimed in claim 9, wherein said phosphor up-converts radiation from IR to visible.

11. An instrument through which an optical fiber is inserted for carrying out a laser treatment procedure, said instrument being separate from the optical fiber, wherein a part of the instrument is provided with a phosphorescent material to provide an indication of a condition at the treatment site, said indication being a light emission by the phosphorescent material that is distinguishable from treatment radiation at the treatment site.

12. An instrument as claimed in claim 11, wherein the instrument part is coated or painted with the phosphorescent material.

13. An instrument as claimed in claim 11, wherein the instrument part is made of a material in which the phosphorescent material has been mixed.

14. An instrument as claimed in claim 11, wherein the instrument is a laser delivery instrument or an introducer.

15. An instrument as claimed in claim 11, wherein the phosphorescent material is a rare-earth nano-phosphor that emits light in visible or near-visible wavelengths.

16. A laser delivery fiber for use during laser treatment procedures, wherein a cladding or buffer of the fiber is provided with a phosphorescent material that is mixed into, or coated or painted onto, a material of the cladding or buffer to provide an indication of a condition at the treatment site, said indication being a light emission by the phosphorescent material that is distinguishable from treatment radiation at the treatment site.

17. A laser delivery fiber as claimed in claim 16, wherein the cladding or buffer is coated or painted with the phosphorescent material.

18. A laser delivery fiber as claimed in claim 16, wherein the phosphorescent material is mixed into the material of the cladding or buffer.

19. A laser delivery fiber as claimed in claim 16, wherein the phosphorescent material is a rare-earth nano-phosphor that emits light in visible or near-visible wavelengths.

* * * * *